US009575085B2

(12) United States Patent
Setomaru et al.

(10) Patent No.: US 9,575,085 B2
(45) Date of Patent: Feb. 21, 2017

(54) AUTOMATIC ANALYSIS DEVICE

(71) Applicant: HITACHI HIGH-TECHNOLOGIES CORPORATION, Tokyo (JP)

(72) Inventors: Takeshi Setomaru, Tokyo (JP); Masato Ishizawa, Tokyo (JP); Hideyasu Chiba, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/760,806

(22) PCT Filed: Jan. 24, 2014

(86) PCT No.: PCT/JP2014/051545
§ 371 (c)(1),
(2) Date: Jul. 14, 2015

(87) PCT Pub. No.: WO2014/119486
PCT Pub. Date: Aug. 7, 2014

(65) Prior Publication Data
US 2015/0346230 A1 Dec. 3, 2015

(30) Foreign Application Priority Data
Feb. 1, 2013 (JP) ................. 2013-018503

(51) Int. Cl.
*G01N 35/02* (2006.01)
*G01N 35/10* (2006.01)
(Continued)

(52) U.S. Cl.
CPC .............. *G01N 35/025* (2013.01); *G01N 1/14* (2013.01); *G01N 21/11* (2013.01);
(Continued)

(58) Field of Classification Search
CPC ............... G01N 35/025; G01N 2035/0439; G01N 2035/0441; G01N 2035/00316
See application file for complete search history.

(56) References Cited

U.S. PATENT DOCUMENTS

| 6,413,475 B2 | 7/2002 | Ishizawa et al. |
| 2002/0009393 A1 | 1/2002 | Ishizawa et al. |

(Continued)

FOREIGN PATENT DOCUMENTS

| JP | 2000-131328 A | 5/2000 |
| JP | 2002-071696 A | 3/2002 |

(Continued)

OTHER PUBLICATIONS

Machine-generated English translation of JP 2008-216173 to Toshiba Corp., Sep. 18, 2008.*

(Continued)

*Primary Examiner* — P. Kathryn Wright
(74) *Attorney, Agent, or Firm* — Mattingly & Malur, PC

(57) ABSTRACT

In an automatic analysis device, when an external force acts on a probe guard 26 in a horizontal direction, the probe guard 26 moves in a direction escaping from the external force around a center portion 47 of a test body container installing mechanism 1, and the probe guard 26 is separated from a fixed position. An outer circumferential wall 29 of the probe guard 26 invades a test body sampling mechanism track 28, and thus a risk that a sampling nozzle 23 of a test body sampling mechanism 5 invades the test body container installing mechanism 1 is avoided by the outer circumferential wall 29. When the probe guard 26 is separated from the fixed position, this is detected, and thus the operation of the test body sampling mechanism 5 and the test body container installing mechanism 1 is stopped.

15 Claims, 11 Drawing Sheets

(51) Int. Cl.
    *G01N 1/14*   (2006.01)
    *G01N 21/11*  (2006.01)
    *G01N 35/00*  (2006.01)
    *G01N 35/04*  (2006.01)
(52) U.S. Cl.
    CPC ....... *G01N 35/00584* (2013.01); *G01N 35/02* (2013.01); *G01N 2035/00316* (2013.01); *G01N 2035/0439* (2013.01); *G01N 2035/0441* (2013.01)

(56) References Cited

U.S. PATENT DOCUMENTS

2002/0025275 A1* 2/2002 Oonuma .............. G01N 35/025
                                                    422/64
2004/0208787 A1* 10/2004 Takahashi .............. G01N 35/02
                                                    422/64

FOREIGN PATENT DOCUMENTS

| JP | 2004-101292 A | 4/2004 |
| JP | 2006-284609 A | 10/2006 |
| JP | 2008216173 A * | 9/2008 |
| JP | 2010-091427 A | 4/2010 |

OTHER PUBLICATIONS

International Search Report of PCT/JP2014/051545.
International Preliminary Report on Patentability received in corresponding International Application No. PCT/JP2014/051545 dated Aug. 13, 2015.
Extended European Search Report received in corresponding European Application No. 14745842.6 dated Sep. 14, 2016.

* cited by examiner

AUTOMATIC ANALYSIS DEVICE

TECHNICAL FIELD

The present invention relates to an automatic analysis device analyzing components in a biological sample such as blood and urine.

BACKGROUND ART

In an automatic analysis device for clinical inspections, a probe is mounted in order to suction or discharge a test body and a test reagent. The probe has a thin tip end and a sharp shape in order to dispense a small amount of test body and test reagent.

In the automatic analysis device, a structure or a countermeasure for reducing a contact risk with a probe tip end portion is required in order to ensure safety of an operator. As an example thereof is a probe guard which is a component disposed in the vicinity of a track of the probe in order to limit access to the probe tip end portion or to call attention to the probe tip end portion.

In PTL 1, as the probe guard, a test body tentacle prevention plate for guarding a finger of the operator from a sample probe is disclosed. The test body tentacle prevention plate is in the shape of a flat plate, and a vertical wall preventing the sample probe from being in contact with the finger of the operator is formed on the flat plate. Then, the test body tentacle prevention plate has a structure in which when the operator presses the test body tentacle prevention plate to an upper portion by using a hand, the test body tentacle prevention plate is moved to the upper portion of a sample disc while being rotated, and this is detected, and thus the movement of the sample probe is stopped.

CITATION LIST

Patent Literature

PTL 1: JP-A-2006-284609

SUMMARY OF INVENTION

Technical Problem

An object of the probe guard disclosed in PTL 1 described above is to limit the access to the probe tip end portion or call attention to the probe tip end portion, and thus the probe guard is fixedly disposed in the vicinity of the track of the probe tip end portion. The probe guard disclosed in PTL 1 is configured to be rotatable to the upper portion of the sample disc, but a sample container is rotatably moved to a lower portion of the probe guard, and thus when the finger of the operator or matter is interposed between the probe guard and the sample disc (a test body container installing mechanism) or between sample containers, a force acts on a direction in which the finger or the matter is further pressed until the probe guard is moved to the upper portion.

An object of the present invention is to realize an automatic analysis device in which even when a hand of an operator or the like is interposed between a probe guard and a test body container installing mechanism, the operation of a test body sampling mechanism and the test body container installing mechanism is able to be stopped without further pressing the hand of the operator.

Solution to Problem

In order to attain the object described above, the present invention is configured as follows.

In an automatic analysis device, a probe guard which is arranged in a test body container arranging mechanism moving a test body container, and includes a guard wall surrounding a test body sampling mechanism when the test body sampling mechanism is positioned on the test body container arranging mechanism, and a retaining unit integrated with the guard wall and retained in an outer circumferential portion of the test body container arranging mechanism to be movable is included, the test body container arranging mechanism includes a probe guard existence detecting sensor detecting a movement of the probe guard from a specific position, and a control unit stops a test body movement operation of the test body container arranging mechanism and a test body suction operation from the test body container of the test body sampling mechanism when the probe guard existence detecting sensor detects that the probe guard is moved from the specific position.

Advantageous Effects of Invention

It is possible to realize the automatic analysis device in which even when the hand of the operator or the like is interposed between the probe guard and the test body container installing mechanism, the operation of the test body sampling mechanism and the test body container installing mechanism is able to be stopped without further pressing the hand of the operator.

DESCRIPTION OF EMBODIMENTS

Figure 1:
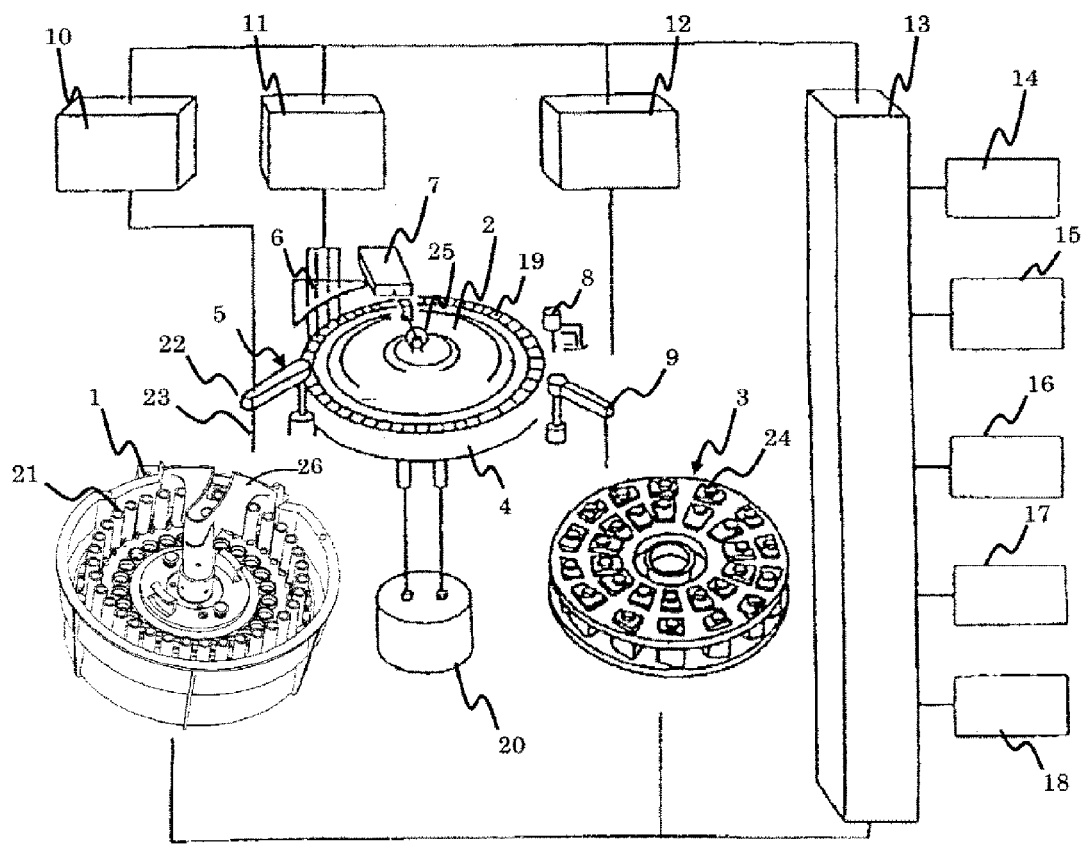
FIG. 1 is a schematic diagram of an overall configuration of an automatic analysis device to which the present invention is applied.

Hereinafter, embodiments of the present invention will be described with reference to the attached drawings. Furthermore, in all of the drawings for illustrating the embodiments of the present invention, the same reference numerals are generally applied to the parts having the same function, and the repeated descriptions thereof will be omitted.

EXAMPLE

FIG. 1 is a schematic diagram of an overall configuration of an automatic analysis device to which the present invention is applied.

In FIG. 1, the automatic analysis device includes a test body container installing mechanism (a test body container arranging mechanism) 1, a reaction vessel mechanism (reaction container arranging mechanism) 2, a test reagent cold storage mechanism (a test reagent container arranging mechanism) 3, a photometer 7, a light source 25, and a touch panel-attached LCD 16.

The reaction vessel mechanism 2 includes a disc which is able to be intermittently rotated, and a plurality of reaction cells 19 formed of a light transmissive material is arranged on the disc along a circumferential direction. The reaction cell 19 is maintained at a predetermined temperature (for example, 37° C.) by a constant temperature vessel 4. The temperature of a fluid in the constant temperature vessel 4 is adjusted by a constant temperature maintaining device 20.

The test body container installing mechanism 1 includes a disc which is rotatably driven, and a plurality of test body containers 21 containing a biological sample such as blood, and urine is arranged, in two rows in an illustrated example, on the disc along the circumferential direction. In addition, a test body sampling mechanism 5 is arranged in the vicinity of the test body container installing mechanism 1. The test body sampling mechanism 5 includes a movable arm 22, and a sampling nozzle 23 attached thereto.

In the test body sampling mechanism 5, the sampling nozzle 23 is suitably moved to a dispensing position by the movable arm 22 at the time of dispensing the sample, a predetermined amount of sample is suctioned from the test body container 21 positioned in a suction position of the test body container installing mechanism 1, and the sample is discharged into the reaction cell 19 which is in a discharge position on the reaction vessel mechanism 2.

In the test reagent cold storage mechanism 3, a plurality of test reagent bottles 24 is arranged along the circumferential direction of the test reagent cold storage mechanism 3. In the test reagent bottle 24, a test reagent solution corresponding to analysis items which are able to be analyzed by the automatic analysis device is contained.

In addition, in the vicinity of the test reagent cold storage mechanism 3, a test reagent pipetting mechanism 9 configuring a mechanism which is approximately identical to the test body sampling mechanism 5 is arranged. When a test reagent is dispensed, the test reagent is suctioned from a reagent bottle 24 corresponding to inspection items which is positioned in a test reagent receiving position on the reaction vessel mechanism 2 and is discharged into the corresponding reaction cell 19 by a pipette nozzle provided in the test reagent pipetting mechanism 9.

A stirring mechanism 8 is arranged in a position surrounded by the reaction vessel mechanism 2, the test reagent cold storage mechanism 3, and the test reagent pipetting mechanism 9. The reaction of a mixed liquid of the sample and the test reagent contained in the reaction cell 19 is promoted by being stirred using the stirring mechanism 8.

Here, the light source 25 is arranged in the vicinity of the center portion of the reaction vessel mechanism 2, the photometer 7 is arranged on an outer circumference side of the reaction vessel mechanism 2, and a row of reaction cells 19 which has been stirred is rotatably moved to pass through a photometric position interposed between the light source 25 and the photometer 7. Furthermore, the light source 25 and the photometer 7 configure a light detection system. The photometer 7 is a multi-wavelength photometer detecting transmissive light or scattering light.

A reaction solution of the sample and the test reagent in each of the reaction cells 19 is subjected to photometry whenever the solution passes over the front of the photometer 7 during a rotation operation of the reaction vessel mechanism 2. An analog signal of the scattering light measured in each sample is input to a Log conversion and A/D converter 15 through an interface 13. The used reaction cell 19 is able to be repeatedly used by cleaning the inside thereof using a reaction cell cleaning mechanism 6 arranged in the vicinity of the reaction vessel mechanism 2.

Next, a control system and a signal processing system of the automatic analysis device illustrated in FIG. 1 will be simply described.

The touch panel-attached LCD 16 is connected to a sample dispensing control unit 10, a test reagent dispensing control unit 12, and a cleaning water pump 11 through the interface 13. The touch panel-attached LCD 16 transmits a command to the sample dispensing control unit 10, and controls a dispensing operation of the sample. In addition, the touch panel-attached LCD 16 transmits a command to the test reagent dispensing control unit 12.

A printer 17 for printing, and a storage medium 18 are connected to the touch panel-attached LCD 16. The storage medium 18, for example, is configured of a hard disk memory or an external memory. In the storage medium 18, information such as a display level of each screen, analysis parameters, requested contents of analysis items, a calibration result, and an analysis result is stored. A microcomputer (a control unit) 14 is connected to the test body container installing mechanism 1, the reaction vessel mechanism 2, the test reagent cold storage mechanism 3, the test body sampling mechanism 5, the test reagent pipetting mechanism 9, the sample dispensing control unit 10, the test reagent dispensing control unit 12, and the cleaning water pump 11 through the interface 13, and controls the operation thereof.

Next, an analysis operation of the sample in the automatic analysis device of FIG. 1 will be described. The analysis parameters relevant to items which are able to be analyzed by the automatic analysis device are input in advance through an information input device such as the touch panel-attached LCD 16, and are stored in the storage medium 18. A manipulator selects inspection items requested for each sample by using a manipulation function screen.

At this time, information such as a patient ID is also input from the touch panel-attached LCD 16. In order to analyze the inspection items indicated with respect to each sample, the sampling nozzle 23 of the test body sampling mechanism 5 dispenses a predetermined amount of the sample from the test body container 21 to the reaction cell 19 according to the analysis parameters.

The reaction cell 19 to which the sample is dispensed is transported by rotating the reaction vessel mechanism 2, and is stopped at the test reagent receiving position. The pipette nozzle of the test reagent pipetting mechanism 9 dispenses a predetermined amount test reagent solution to the reaction cell 19 according to the analysis parameters of the corresponding inspection items. The dispensing order of the sample and the test reagent may be contrary to this example such that the test reagent is dispensed before the sample is dispensed.

After that, the sample and the test reagent are stirred by the stirring mechanism 8, and are mixed. When the reaction cell 19 passes over the photometric position, transmissive light or scattering light of the reaction solution is subjected to photometry by the photometer 7. The transmissive light or the scattering light which is subjected to photometry is converted into a numerical value proportional to light intensity by the Log conversion and A/D converter 15, and is imported into the storage medium 18 through the touch panel-attached LCD 16.

Concentration data is calculated by using the converted numerical value on the basis of a standard curve which is measured in advance by an analysis method designated for each of the inspection items. Component concentration data as an analysis result of the inspection items is output to the printer 17.

Before the measurement operations described above are executed, the manipulator sets various parameters which are required for analysis measurement or registers a specimen through the touch panel-attached LCD 16. In addition, the manipulator confirms the analysis result from the measurement through the touch panel-attached LCD 16 or the printing from the printer 17.

In FIG. 1, a probe guard 26 is attached to the test body container installing mechanism 1.

Figure 2:
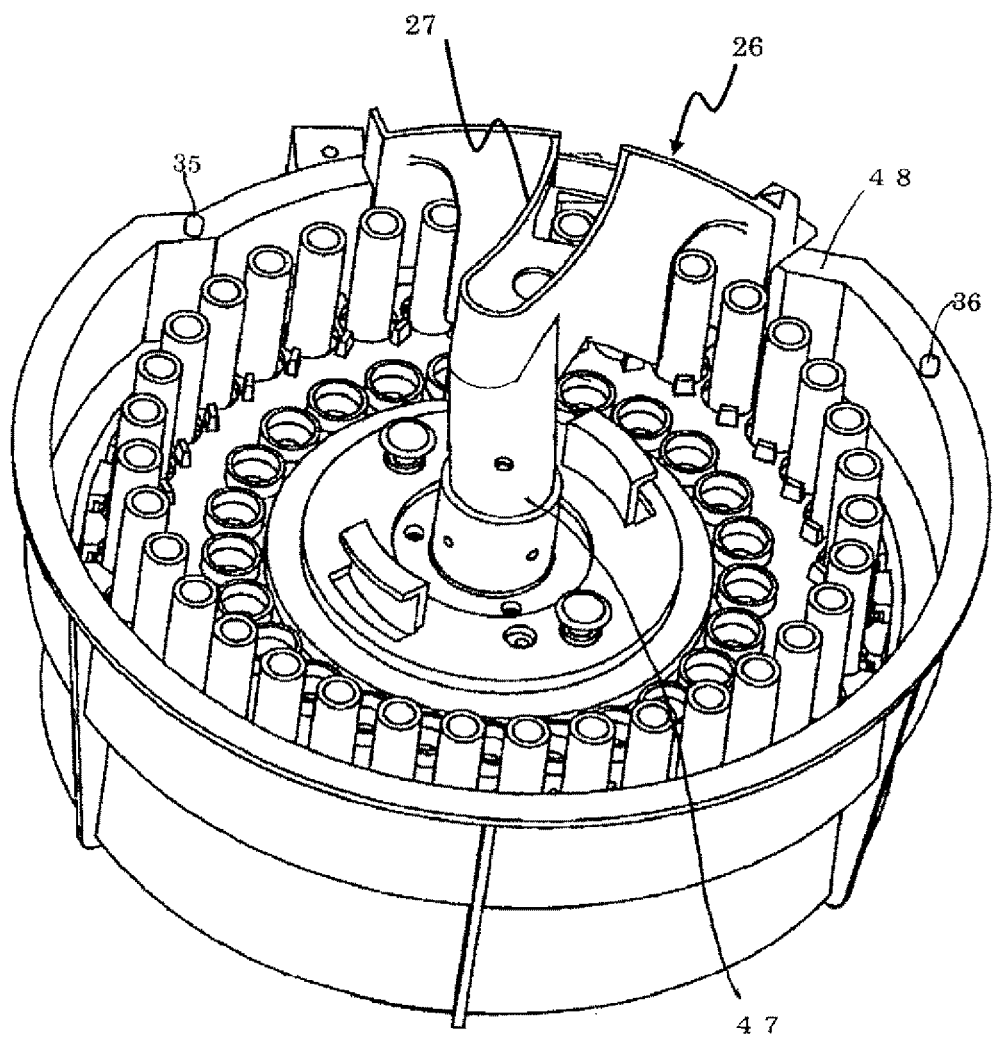
FIG. 2 is a perspective view of a test body container installing mechanism and a probe guard in an example of the present invention.

FIG. 2 is a perspective view of the test body container installing mechanism 1 and the probe guard 26. In FIG. 2, the probe guard 26 is positioned on an upper portion of the test body container installing mechanism 1 by being supported on a center portion 47 of the test body container installing mechanism 1 and an outer circumferential portion 48. In the probe guard 26, a guard wall 27 for blocking access to the test body sampling mechanism 5 is formed along a track of the test body sampling mechanism 5. The guard wall 27 is in parallel with a movement track of the test body sampling mechanism 5 on the test body container installing mechanism 1, and is a wall-like member erected in a vertical direction.

The probe guard 26 is movable along the outer circumferential portion 48, but probe guard stoppers 35 and 36 are formed in the outer circumferential portion 48, and thus a movement range of the probe guard 26 is limited. In addition, the position of the probe guard 26 illustrated in FIG. 2 is a fixed position in a normal state, and in a state of the fixed position, the sample nozzle 23 passes through the guard walls 27, and is further moved to a lower direction, and thus accesses the test body container 21.

The outer circumferential portion 48 of the probe guard 26 is in the shape where the outer circumferential portion 48 is moved up by being inclined towards the probe guard stopper 35 from the fixed position in the normal state. In addition, the outer circumferential portion 48 is in the shape where the outer circumferential portion 48 is moved up by being inclined towards the probe guard stopper 36 from the fixed position in the normal state.

Figure 3:
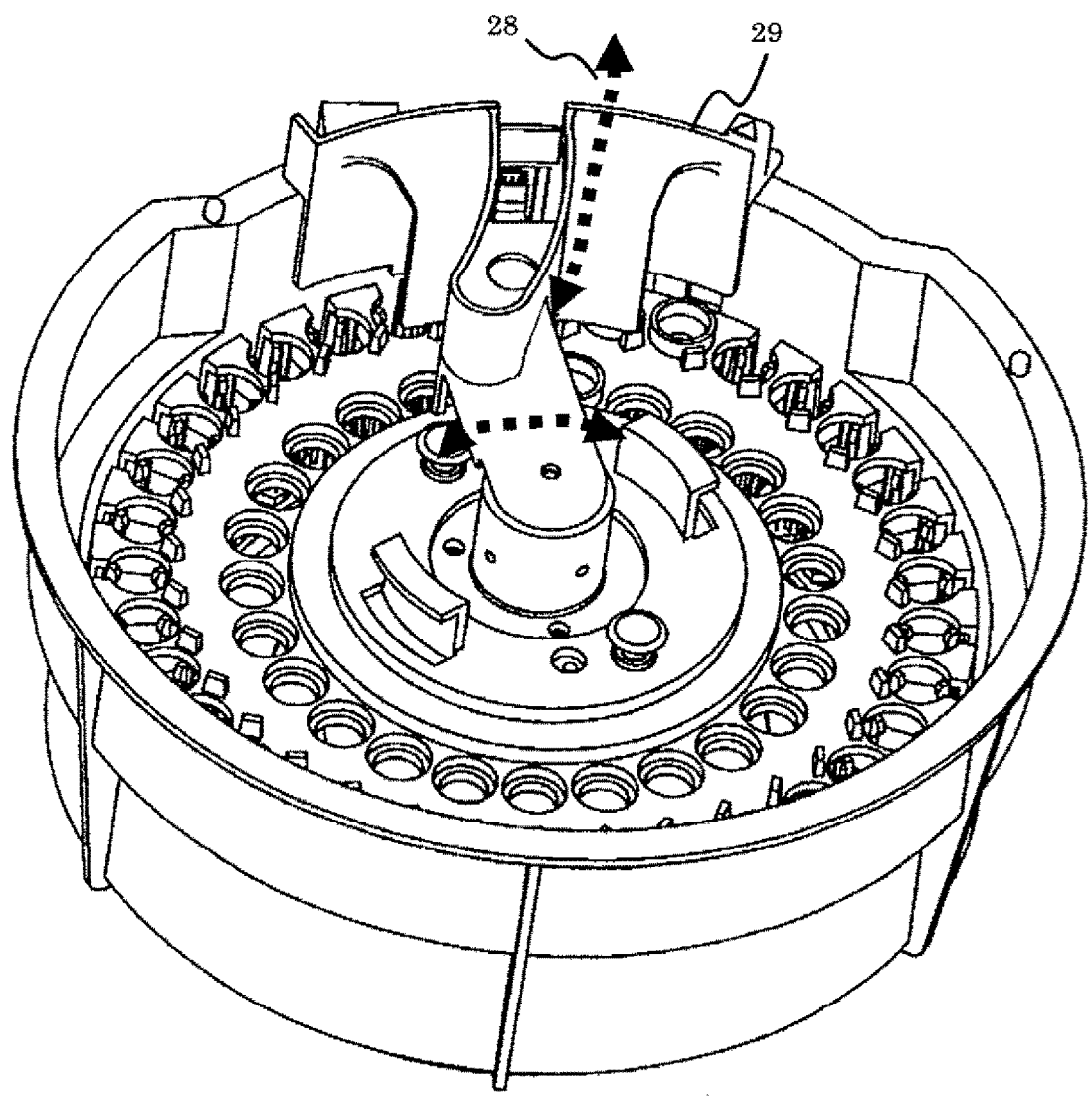
FIG. 3 is a diagram illustrating a state when the probe guard is separated from a fixed position due to an external force in an example of the present invention.

FIG. 3 is a diagram illustrating a state when the probe guard 26 is separated from the fixed position due to an external force. When an external force acts on the probe guard 26 in a horizontal direction, the probe guard 26 is moved in a direction escaping from the external force around the center portion 47 of the test body container installing mechanism 1. Then, the probe guard 26 is separated from the fixed position. At this time, an outer circumferential wall 29 of the probe guard 26 invades a test body sampling mechanism track 28 which is the movement locus of the sampling nozzle 23, and thus a risk that the sampling nozzle 23 of the test body sampling mechanism 5 invades the test body container installing mechanism 1 is able to be avoided by the outer circumferential wall 29.

In addition, as described later, when the probe guard 26 is separated from the fixed position, this is detected, and thus the operation of the test body sampling mechanism 5 and the test body container installing mechanism 1 is stopped.

In a case where the probe guard 26 is separated from the fixed position due to the external force, when the external force is excluded, the probe guard 26 is able to automatically return to the fixed position. This is because the outer circumferential portion 48 is in the shape of being inclined towards the fixed position.

Figure 4:
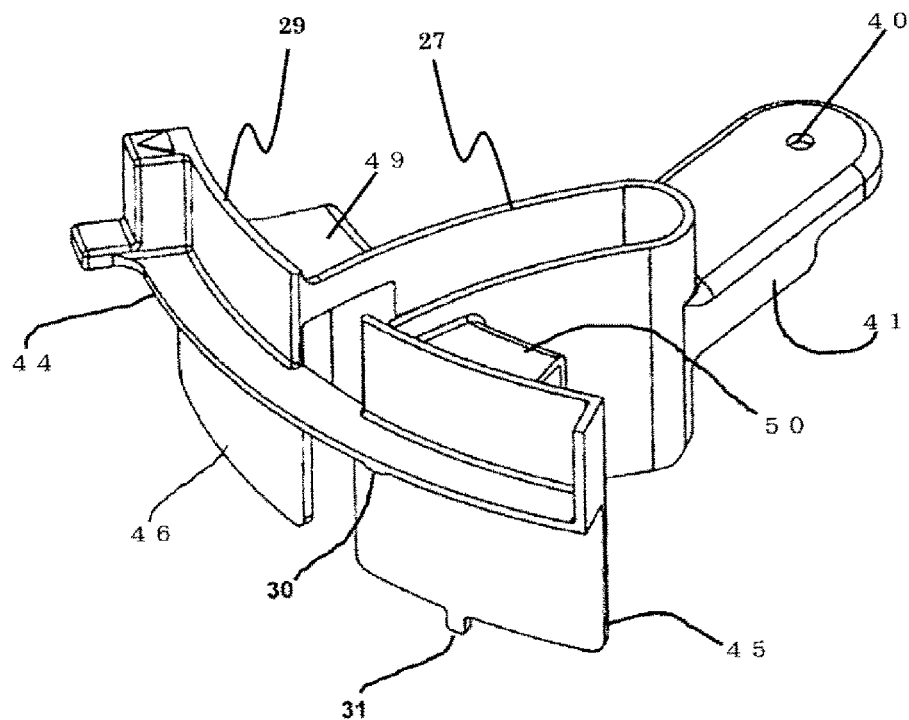
FIG. 4 is a perspective view of the probe guard which is an example of the present invention.
Figure 5:
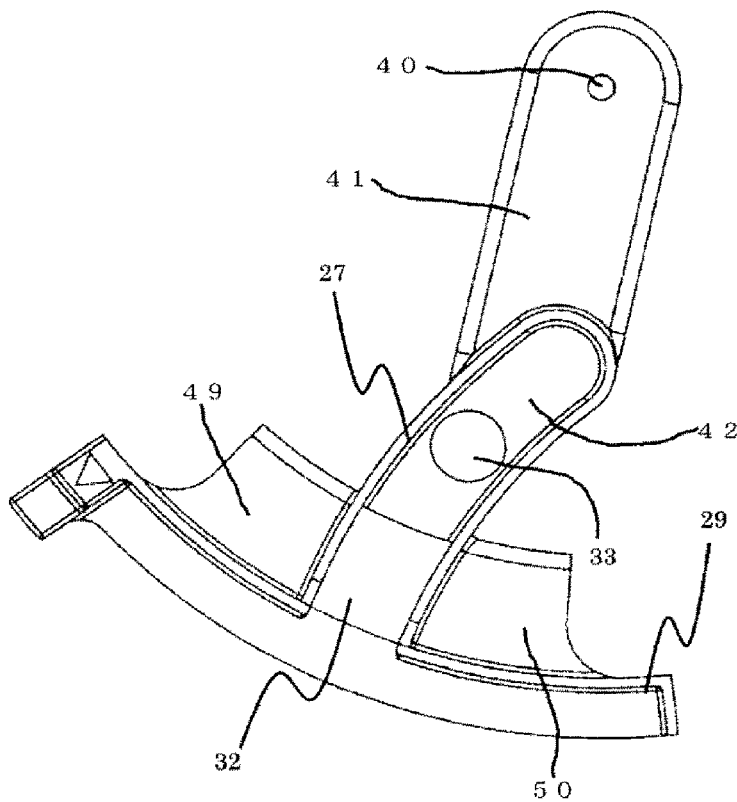
FIG. 5 is a top view of the probe guard which is an example of the present invention.
Figure 6:
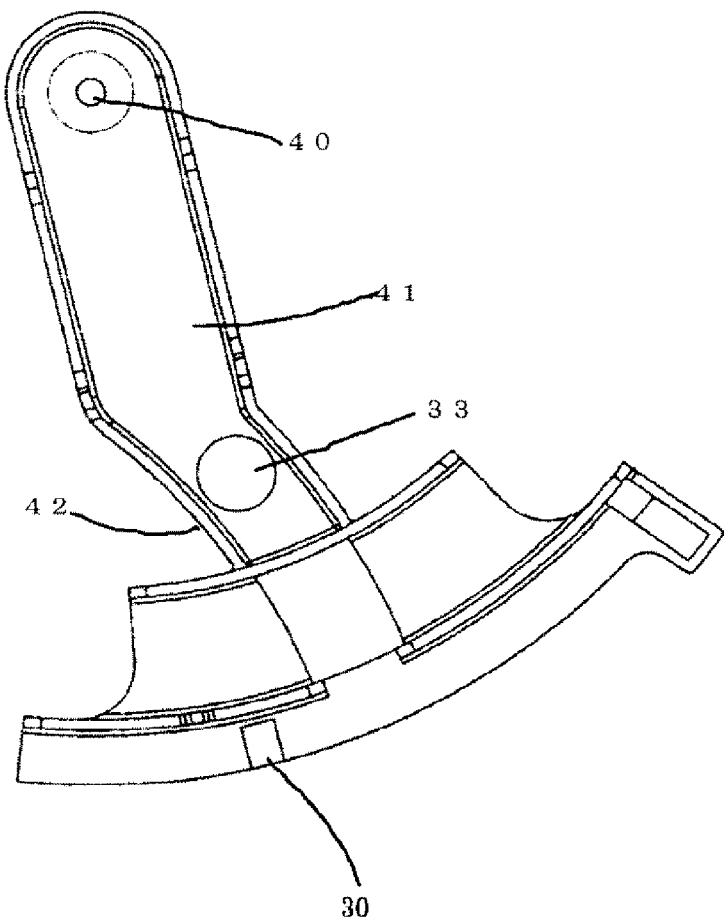
FIG. 6 is a bottom view of the probe guard which is an example of the present invention.
Figure 7:
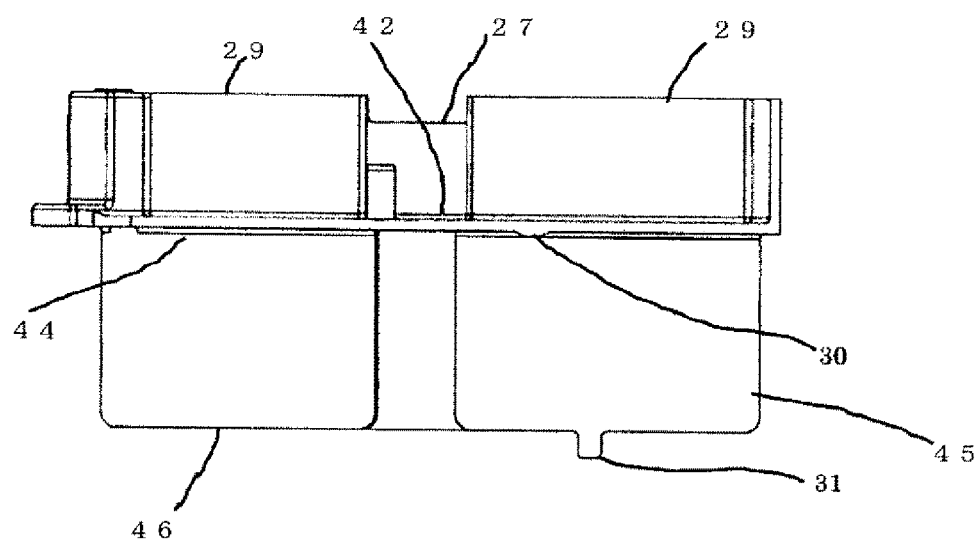
FIG. 7 is a front view of the probe guard which is an example of the present invention.

The probe guard 26 is able to be detached from the test body container installing mechanism 1. FIG. 4 is a perspective view of the probe guard 26 in a state of being detached from the test body container installing mechanism 1. In addition, FIG. 5 is a top view of the probe guard 26, and FIG. 6 is a bottom view of the probe guard 26. Further, FIG. 7 is a front view of the probe guard 26.

In FIG. 4, FIG. 5, FIG. 6, and FIG. 7, the probe guard 26 includes a hole 40 attached to the center portion 47 of the test body container installing mechanism 1, and in the probe guard 26, a first arm portion 41 extending in the horizontal direction, a second arm portion 42 including the guard wall 27 extending from an end portion of the first arm portion 41 in the vertical direction, an arc-like outer circumferential wall 29 around the hole 40 which is continued from the guard wall 27, inversed L-shaped container cover portions 49 and 50 protruding from the outer circumferential wall 29 towards the hole 40, and a retaining unit 44 extending in a direction vertical to the outer circumferential wall 29 which is continued from the outer circumferential wall 29.

The retaining unit 44 is placed on the outer circumferential portion 48 of the test body container installing mechanism 1. In a lower surface portion of the retaining unit 44, a protrusion-like disposition positioning unit 30 is formed. The disposition positioning unit 30 is inserted into a probe guard positioning groove 37 (described later) formed in the outer circumferential portion 48, and is positioned in the fixed position of the probe guard 26.

In addition, the outer circumferential wall 29 includes vertical wall portions 45 and 46 extending towards a lower portion, and a probe guard existence detecting unit 31 protruding towards the lower portion is formed in a lower edge portion of the vertical wall portion 45. The probe guard existence detecting unit 31 is detected by a probe guard existence detecting sensor 39 described later, and thus it is detected whether or not the probe guard 26 is arranged in the fixed position.

In addition, dispensing ports 32 and 33 are formed in the second arm portion 42, and the sample nozzle 23 of the test body sampling mechanism 5 is inserted into the test body container through the dispensing ports 32 and 33.

Figure 8:
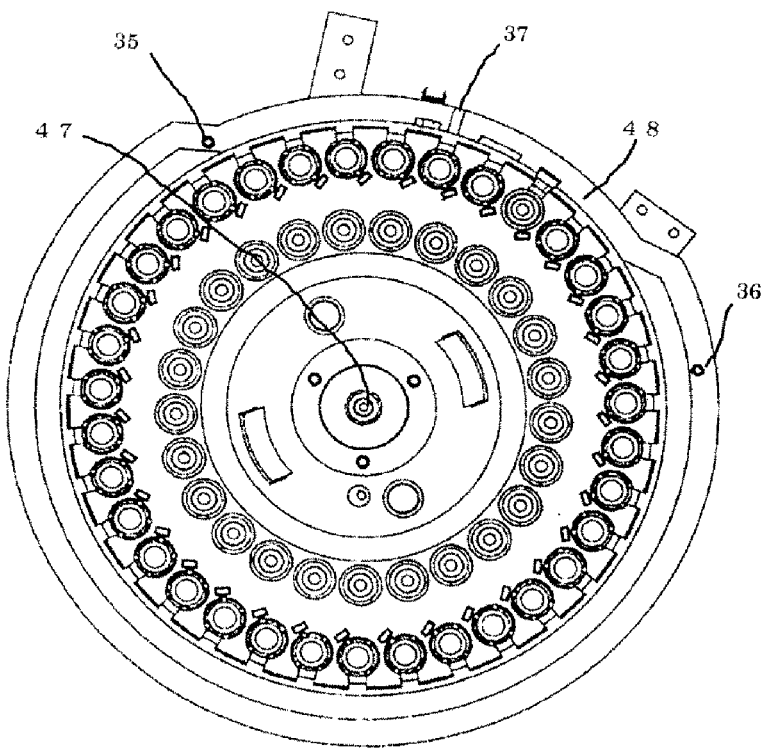
FIG. 8 is a top view of the test body container installing mechanism before the probe guard which is an example of the present invention is disposed.
Figure 9:
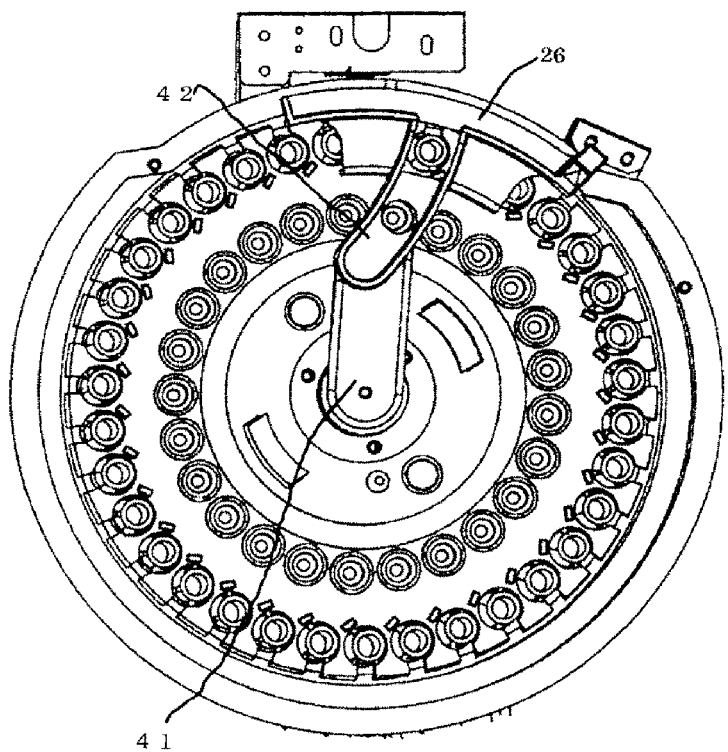
FIG. 9 is a top view of the test body container installing mechanism in a state where the probe guard which is an example of the present invention is disposed.

FIG. 8 is a top view of the test body container installing mechanism 1 before the probe guard 26 is disposed, and FIG. 9 is a top view of the test body container installing mechanism 1 in a state where the probe guard 26 is disposed. In addition, FIG. 10 is a perspective view of the test body container installing mechanism 1 before the probe guard 26 is disposed, and FIG. 11 is a perspective view of the test body container installing mechanism 1 in the state where the probe guard 26 is disposed.

As illustrated in FIG. 8, the probe guard positioning groove 37 is formed on the outer circumferential portion 48, and the disposition positioning unit 30 of the probe guard 26 is inserted to the probe guard positioning groove 37 and is positioned, and thus, as illustrated in FIG. 9, the probe guard 26 is arranged in the test body container installing mechanism 1.

Figure 10:
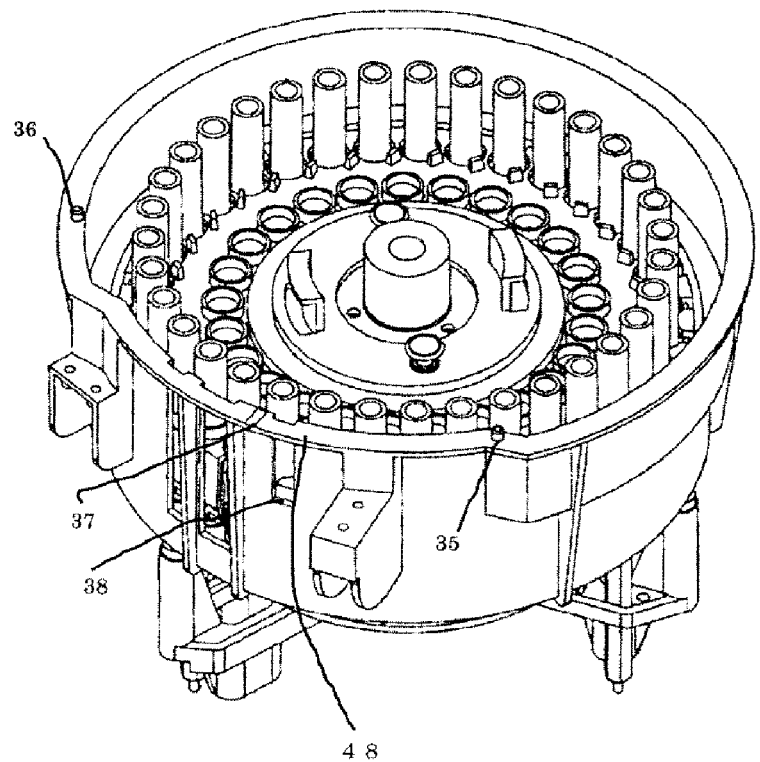
FIG. 10 is a perspective view of the test body container installing mechanism before the probe guard which is an example of the present invention is disposed.
Figure 11:
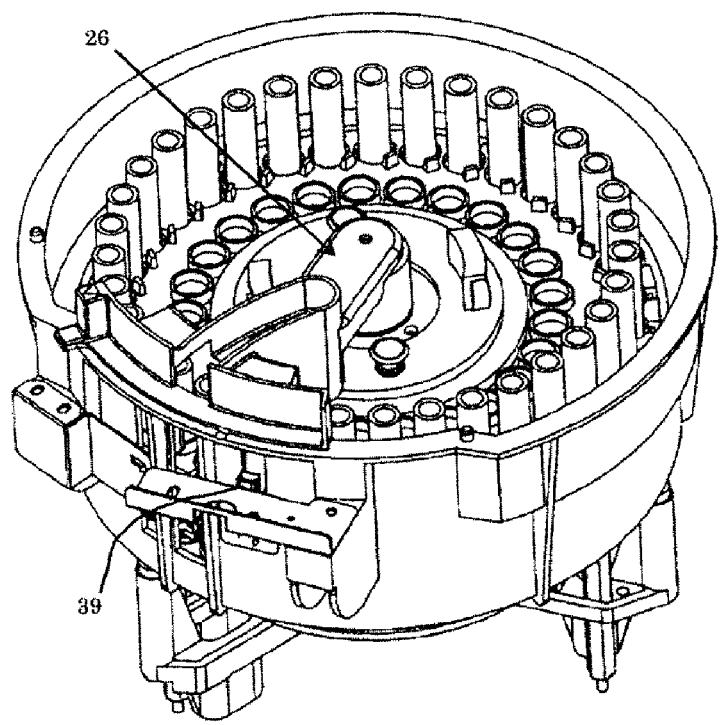
FIG. 11 is a perspective view of the test body container installing mechanism in the state where the probe guard which is an example of the present invention is disposed.

In FIG. 10, a window for detecting probe guard existence 38 is formed in the test body container installing mechanism 1. In addition, as illustrated in FIG. 11, the probe guard existence detecting sensor 39 is attached to the test body container installing mechanism, and the probe guard existence detecting unit 31 of the probe guard 26 arranged in the fixed position is detected through the window for detecting the probe guard existence 38. Furthermore, in FIG. 10, the probe guard existence detecting sensor 39 is not illustrated.

Figure 12:
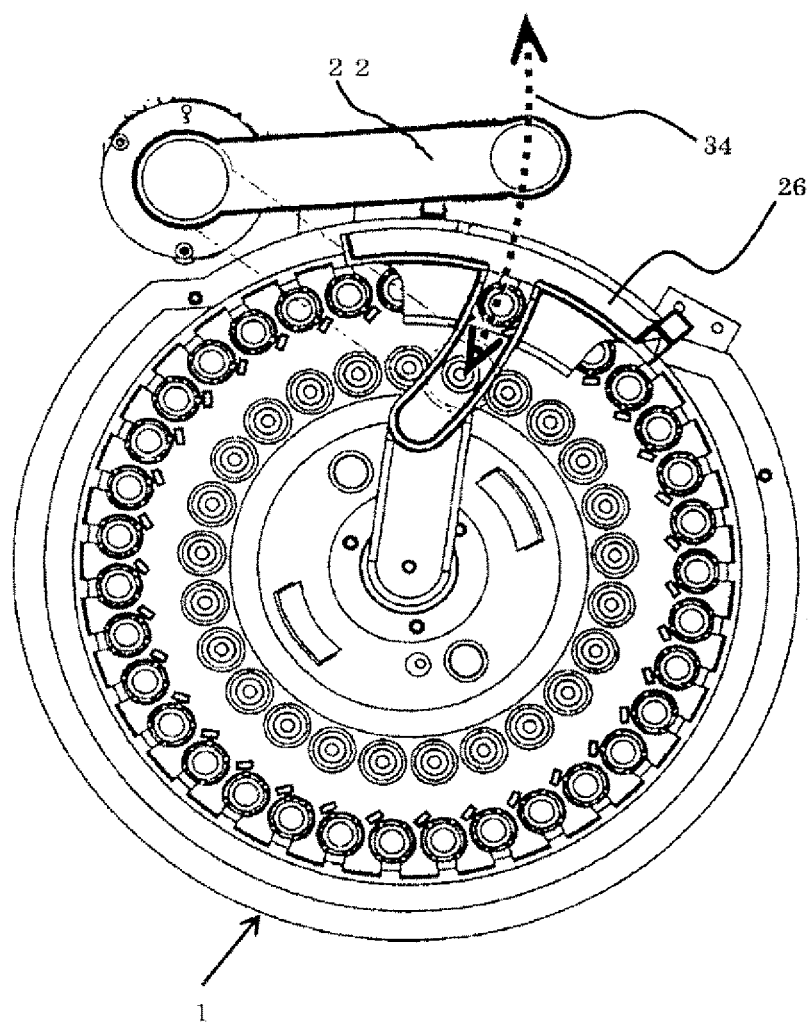
FIG. 12 is a diagram illustrating a movement track of a sampling arm in a state where the probe guard is arranged in a fixed position of the test body container installing mechanism.
Figure 13:
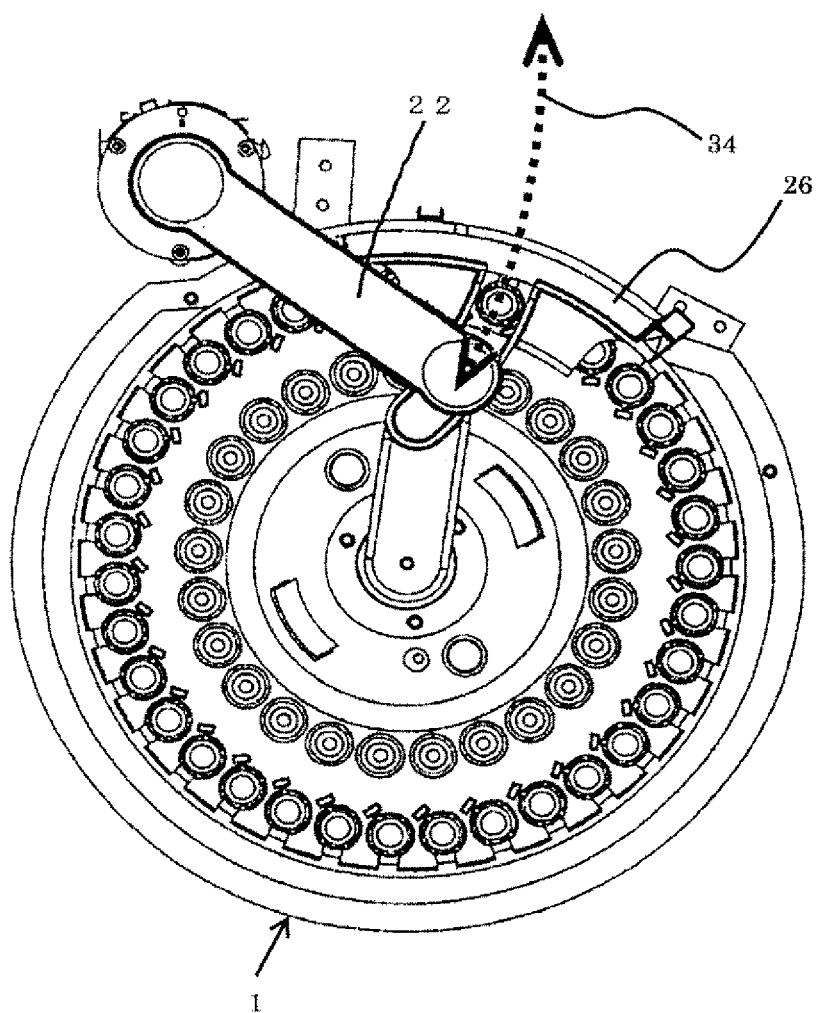
FIG. 13 is a diagram illustrating the movement track of the sampling arm in the state where the probe guard is arranged in the fixed position of the test body container installing mechanism.

FIG. 12 and FIG. 13 are diagrams illustrating a movement track 34 of the movable arm 22 of the test body sampling mechanism 5 in a state where the probe guard 26 is arranged in the fixed position of the test body container installing mechanism 1. As illustrated in FIG. 12 and FIG. 13, the movable arm 22 is moved, and thus the sampling nozzle 23 of the movable arm 22 is guarded by the guard wall 27, and the manipulator is prevented from being in contact with the sampling nozzle 23.

Figure 14:
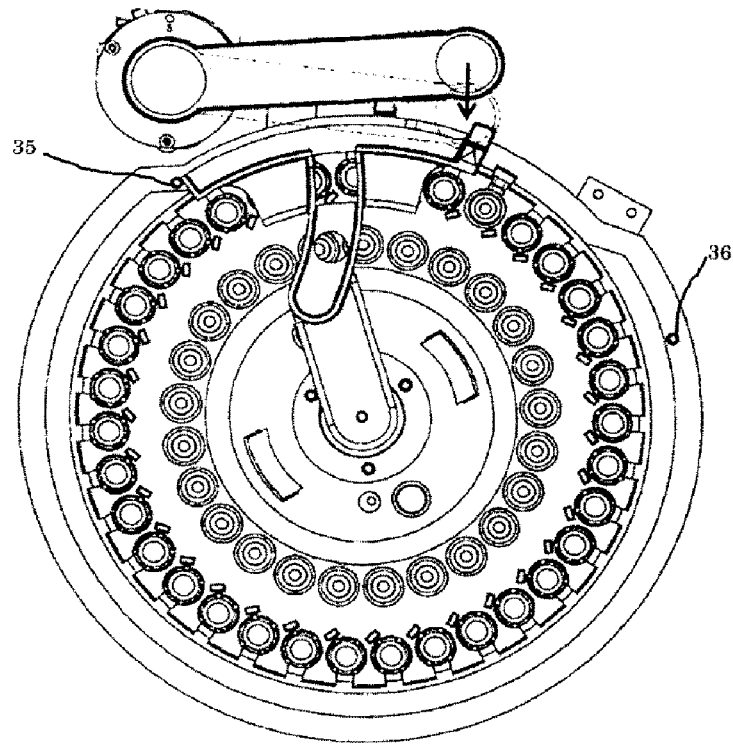
FIG. 14 is a diagram illustrating a state where the probe guard is moved from the fixed position.
Figure 15:
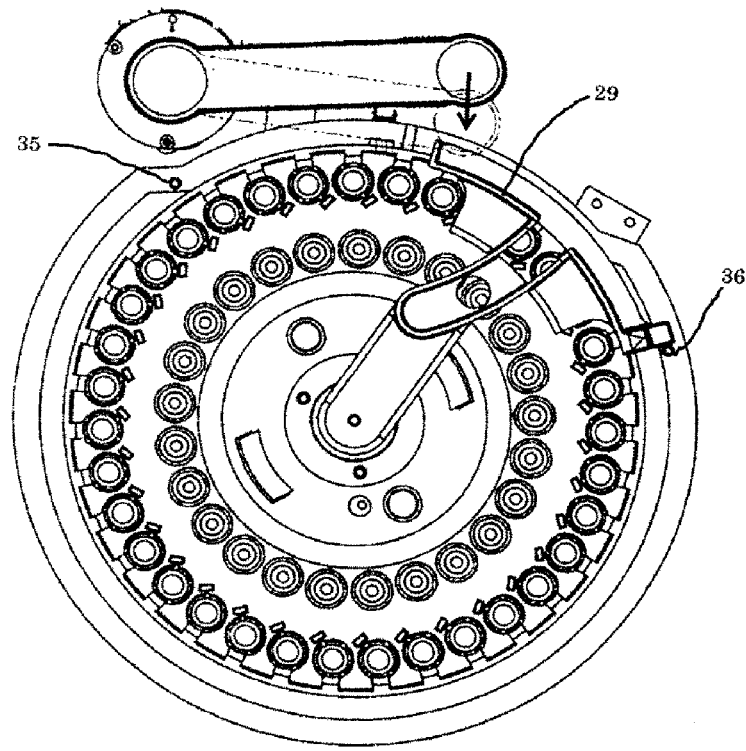
FIG. 15 is a diagram illustrating the state where the probe guard is moved from the fixed position.

FIG. 14 and FIG. 15 are diagrams illustrating a state where, for example, the hand of the manipulator is in contact with the probe guard 26, and thus the probe guard 26 is moved from the fixed position. FIG. 14 illustrates a case where the probe guard is moved in a counterclockwise direction, and FIG. 15 illustrates a case where the probe guard 26 is moved in a clockwise direction.

In the state illustrated in FIG. 14 and FIG. 15, the probe guard existence detecting sensor 39 detects that the probe guard 26 is not arranged in the fixed position, and transmits the detection result to the microcomputer 14. The microcomputer 14 receives a detection signal that there is no probe guard from the probe guard existence detecting sensor 39, and stops a test body container rotation operation of the test body container installing mechanism 1 and stops the operation of the test body sampling mechanism 5.

Even when the probe guard is in contact with the stopper 35 or 37, the positions of the stoppers 35 and 36 are determined such that the movement of the movable arm 22 is able to be stopped by the outer circumferential wall 29.

Figure 16:
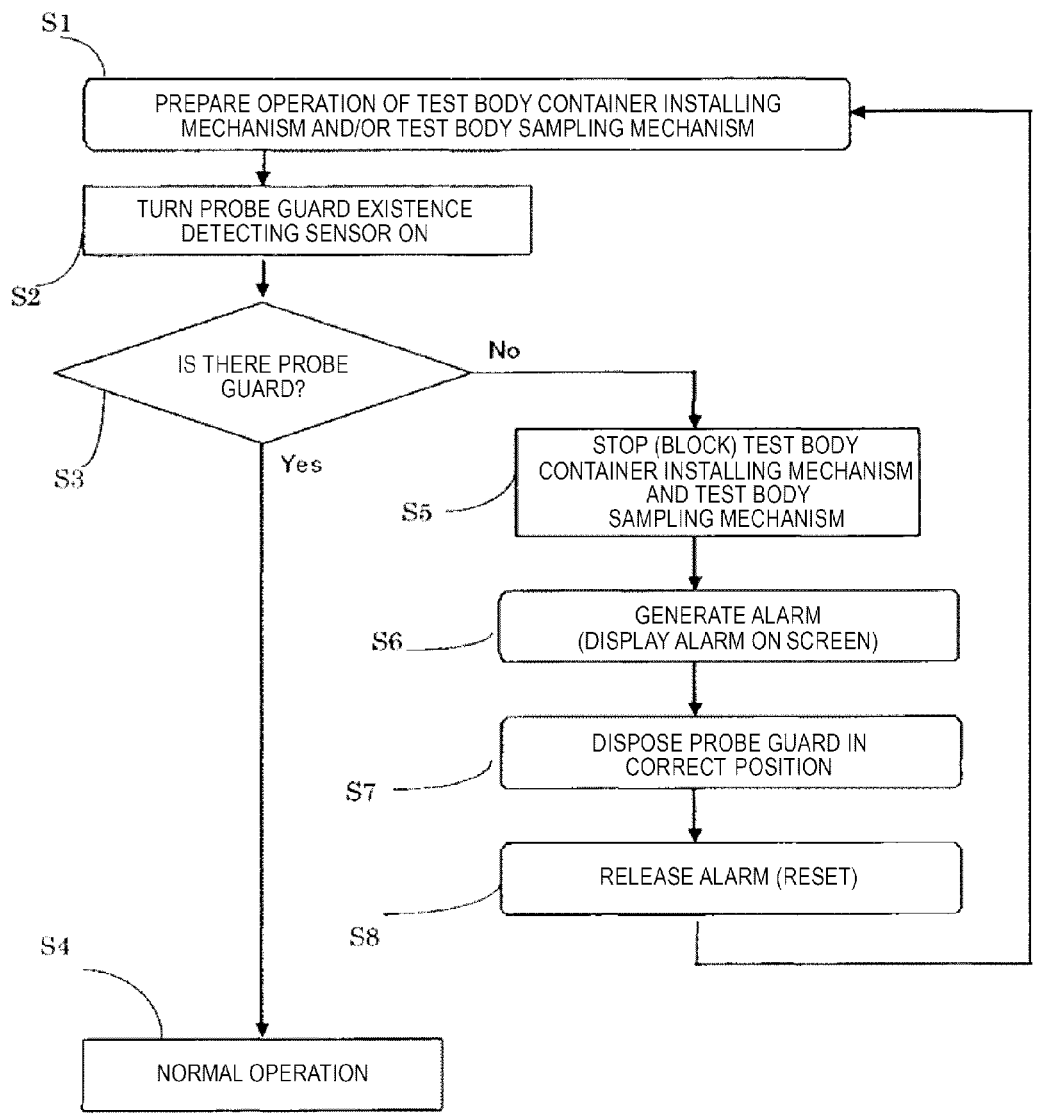
FIG. 16 is an operation flowchart of the test body container installing mechanism and a test body sampling mechanism in an example of the present invention.

FIG. 16 is an operation flowchart of the test body container installing mechanism 1 and the test body sampling mechanism 5.

In Step S1 of FIG. 16, operation preparation (disposition of the container of the test body, and confirmation of the arrangement of the disposed test body) of the test body container installing mechanism 1 and operation preparation of the test body sampling mechanism 5 are performed. Then, in Step S2, the probe guard existence detecting sensor 39 is turned ON, and a detection operation starts.

Next, in Step S3, the microcomputer 14 determines whether or not the probe guard 26 is in the fixed position according to a detection signal from the probe guard existence detecting sensor 39. When it is determined that the probe guard 26 is positioned in the fixed position, in Step S4, the microcomputer 14 controls each unit and performs a normal operation.

In Step S3, when it is determined that the probe guard 26 is not positioned in the fixed position, the process proceeds to Step S5. Then, in Step S5, the microcomputer 14 stops the rotary driving of the disc of the test body container installing mechanism 1, and also stops the operation of the test body sampling mechanism 5.

Subsequently, in Step S6, the microcomputer 14 displays a screen generating an alarm on the LCD 16 which is a display. At this time, a sound is also able to be generated. Then, in Step S7, when the probe guard existence detecting sensor 39 detects that the probe guard 26 returns to the fixed position, in Step S8, the alarm is released, and the process returns to Step S1.

As described above, according to an example of the present invention, the probe guard 26 is movable in parallel with a movement direction of the test body container of the test body container installing mechanism 1, and when the probe guard 26 is moved from the fixed position, this is detected, and thus the rotary driving of the disc of the test body container installing mechanism 1 is stopped, and the operation of the test body sampling mechanism 5 is also stopped.

Therefore, the automatic analysis device is realized in which even when the hand of the operator or the like is interposed between the probe guard and the test body container installing mechanism, the operation of the test body sampling mechanism and the test body container installing mechanism is able to be stopped without further pressing the hand of the operator.

In addition, the probe guard 26 is able to be detached, but when the device is operated in a state where the probe guard 26 is not arranged in the test body container installing mechanism 1, the probe guard existence detecting sensor 39 detects that the probe guard 26 is not arranged, and thus the alarm may be displayed.

Furthermore, the material of the probe guard 26 may also be a resin and a metal.

REFERENCE SIGNS LIST

1 TEST BODY CONTAINER INSTALLING MECHANISM
2 REACTION VESSEL MECHANISM
3 TEST REAGENT COLD STORAGE MECHANISM
4 CONSTANT TEMPERATURE VESSEL
5 TEST BODY SAMPLING MECHANISM
6 REACTION CELL CLEANING MECHANISM
7 PHOTOMETER
8 STIRRING MECHANISM
9 TEST REAGENT PIPETTING MECHANISM
10 SAMPLE DISPENSING CONTROL UNIT
11 CLEANING WATER PUMP
12 TEST REAGENT DISPENSING CONTROL UNIT
13 INTERFACE
14 MICROCOMPUTER
15 Log CONVERSION AND A/D CONVERTER
16 TOUCH PANEL-ATTACHED LCD
17 PRINTER
18 STORAGE MEDIUM
19 REACTION CELL
20 CONSTANT TEMPERATURE MAINTAINING DEVICE
21 TEST BODY CONTAINER

22 MOVABLE ARM
23 SAMPLING NOZZLE
24 TEST REAGENT BOTTLE
25 LIGHT SOURCE
26 PROBE GUARD
27 GUARD WALL
28 TEST BODY SAMPLING MECHANISM TRACK
29 OUTER CIRCUMFERENTIAL WALL
30 DISPOSITION POSITIONING UNIT
31 PROBE GUARD EXISTENCE DETECTING UNIT
32, 33 DISPENSING PORT
35, 36 PROBE GUARD STOPPER
37 PROBE GUARD POSITIONING GROOVE
38 WINDOW FOR DETECTING PROBE GUARD EXISTENCE
39 SENSOR FOR DETECTING PROBE GUARD EXISTENCE
40 HOLE
41 FIRST ARM PORTION
44 RETAINING UNIT
45, 46 VERTICAL WALL PORTION
47 CENTER PORTION
48 OUTER CIRCUMFERENTIAL PORTION
49, 50 INVERSED L-SHAPED CONTAINER COVER PORTION

The invention claimed is:

1. An automatic analysis device, comprising:
a test body container arranging mechanism in which a test body container is arranged and the arranged test body container is moved;
a test reagent container arranging mechanism in which a test reagent container is arranged;
a reaction container arranging mechanism in which a reaction container for reacting a test body with a test reagent is arranged;
a test body sampling mechanism which suctions the test body from the test body container arranged in the test body container arranging mechanism, and discharges the test body to the reaction container arranged in the reaction container arranging mechanism;
a test reagent sampling mechanism which suctions the test reagent from the test reagent container arranged in the test reagent container arranging mechanism, and discharges the test reagent to the reaction container arranged in the reaction container arranging mechanism;
an optical analyzer which analyzes the test body in the reaction container arranged in the reaction container arranging mechanism;
a control unit which controls operations of the test body container arranging mechanism, the test reagent container arranging mechanism, the reaction container arranging mechanism, the test body sampling mechanism, and the test reagent sampling mechanism; and
a probe guard which is supported by a center portion and an outer circumferential portion of the test body container arranging mechanism and is disposed at a specific position on the test body container arranging mechanism, and the probe guard includes a guard wall that surrounds the test body sampling mechanism when the test body sampling mechanism is positioned over the test body container arranging mechanism, and a retaining unit integrated with the guard wall and which retains the probe guard on the outer circumferential portion of the test body container arranging mechanism to be movable along the outer circumferential portion of the test body container arranging mechanism from the specific position,
wherein the test body container arranging mechanism includes a probe guard existence detecting sensor that detects a movement of the probe guard from the specific position, and
wherein the control unit stops a test body movement operation of the test body container arranging mechanism and a test body suction operation from the test body container of the test body sampling mechanism when the probe guard existence detecting sensor detects that the probe guard is moved along the outer circumferential portion of the test body container arranging mechanism from the specific position.

2. The automatic analysis device according to claim 1, wherein the guard wall of the probe guard extends in a vertical direction to surround a movement track of the test body sampling mechanism over test body container arranging mechanism, and the guard wall further surrounds a dispensing port through which the test body sampling mechanism suctions the test body from the test body container.

3. The automatic analysis device according to claim 1, wherein the probe guard is movable around the center portion of the test body container arranging mechanism from the specific position.

4. The automatic analysis device according to claim 1, wherein a first protrusion is formed in the retaining unit of the probe guard, and a positioning groove to which the first protrusion is inserted is formed in the test body container arranging mechanism to position the probe guard at the specific position.

5. The automatic analysis device according to claim 1, wherein a pair of stoppers disposed on the outer circumferential portion of the test body container arranging mechanism limit a movement range of the probe guard along the outer circumferential portion of the test body container arranging mechanism.

6. The automatic analysis device according to claim 1, wherein the probe guard is attachable to and detachable from the test body container arranging mechanism.

7. The automatic analysis device according to claim 1, further comprising:
a display unit,
wherein the control unit displays an alarm on the display unit when the probe guard existence detecting sensor detects that the probe guard is moved along the outer circumferential portion of the test body container arranging mechanism from the predetermined position.

8. The automatic analysis device according to claim 1, wherein the probe guard includes a second protrusion that extends from below the probe guard into a window of the test body container arranging mechanism when the probe guard is disposed at the specific position, and
wherein the probe guard existence detecting sensor detects that the probe guard is moved along the outer circumferential portion of the test body container arranging mechanism from the specific position when the second protrusion is removed from the window.

9. An automatic analysis device, comprising:
a test body container arranging mechanism in which a test body container is arranged and the arranged test body container is moved;
a test reagent container arranging mechanism in which a test reagent container is arranged;

a reaction container arranging mechanism in which a reaction container for reacting a test body with a test reagent is arranged;

a test body sampling mechanism which suctions the test body from the test body container arranged in the test body container arranging mechanism, and discharges the test body to the reaction container arranged in the reaction container arranging mechanism;

a test reagent sampling mechanism which suctions the test reagent from the test reagent container arranged in the test reagent container arranging mechanism, and discharges the test reagent to the reaction container arranged in the reaction container arranging mechanism;

an optical analyzer which analyzes the test body in the reaction container arranged in the reaction container arranging mechanism;

a control unit which controls operations of the test body container arranging mechanism, the test reagent container arranging mechanism, the reaction container arranging mechanism, the test body sampling mechanism, and the test reagent sampling mechanism; and a probe guard which is supported by a center portion and an outer circumferential portion of the test body container arranging mechanism and is disposed at a specific position on the test body container arranging mechanism, and the probe guard includes a guard wall that surrounds the test body sampling mechanism when the test body sampling mechanism is positioned over the test body container arranging mechanism, and a retaining unit integrated with the guard wall and which retains the probe guard on the outer circumferential portion of the test body container arranging mechanism to be movable along the outer circumferential portion of the test body container arranging mechanism from the specific position, wherein the test body container arranging mechanism includes a probe guard existence detecting sensor that detects a movement of the probe guard from the specific position, wherein a first protrusion is formed on the retaining unit of the probe guard, and a positioning groove to which the first protrusion is inserted is formed in the test body container arranging mechanism to position the probe guard at the specific position, and wherein the control unit stops a test body movement operation of the test body container arranging mechanism and a test body suction operation from the test body container of the test body sampling mechanism when the probe guard existence detecting sensor detects that the probe guard is moved along the outer circumferential portion of the test body container arranging mechanism from the specific position.

10. The automatic analysis device according to claim 9,
wherein the guard wall of the probe guard extends in a vertical direction to surround a movement track of the test body sampling mechanism over test body container arranging mechanism, and the guard wall further surrounds a dispensing port through which the test body sampling mechanism suctions the test body from the test body container.

11. The automatic analysis device according to claim 9,
wherein the probe guard is movable around the center portion of the test body container arranging mechanism from the specific position.

12. The automatic analysis device according to claim 9,
wherein a pair of stoppers disposed on the outer circumferential portion of the test body container arranging mechanism limit a movement range of the probe guard along the outer circumferential portion of the test body container arranging mechanism.

13. The automatic analysis device according to claim 9,
wherein the probe guard is attachable to and detachable from the test body container arranging mechanism.

14. The automatic analysis device according to claim 9, further comprising:
a display unit,
wherein the control unit displays an alarm on the display unit when the probe guard existence detecting sensor detects that the probe guard is moved along the outer circumferential portion of the test body container arranging mechanism from the predetermined position.

15. The automatic analysis device according to claim 9,
wherein the probe guard includes a second protrusion that extends from below the probe guard into a window of the test body container arranging mechanism when the probe guard is disposed at the specific position, and
wherein the probe guard existence detecting sensor detects that the probe guard is moved along the outer circumferential portion of the test body container arranging mechanism from the specific position when the second protrusion is removed from the window.

* * * * *